US011642291B2

(12) United States Patent
Gough et al.

(10) Patent No.: US 11,642,291 B2
(45) Date of Patent: *May 9, 2023

(54) METHODS, COMPOSITIONS AND USES RELATING THERETO

(71) Applicant: INNOSPEC LIMITED, Ellesmere Port (GB)

(72) Inventors: Tony Gough, Chester (GB); Matthew Robert Giles, Chester (GB); Kimberley Elizabeth Griffiths, Rhyl (GB); Nicholas John Dixon, Chester (GB); Ian Malcolm Mcrobbie, Chester (GB)

(73) Assignee: Innospec Limited, Ellesmere Port (GB)

( * ) Notice: Subject to any disclaimer, the term of this patent is extended or adjusted under 35 U.S.C. 154(b) by 176 days.

This patent is subject to a terminal disclaimer.

(21) Appl. No.: 17/034,315

(22) Filed: Sep. 28, 2020

(65) Prior Publication Data

US 2021/0007952 A1 Jan. 14, 2021

Related U.S. Application Data

(62) Division of application No. 16/095,567, filed as application No. PCT/GB2017/051112 on Apr. 21, 2017, now Pat. No. 10,799,440.

(30) Foreign Application Priority Data

Apr. 22, 2016 (GB) ...................................... 1607043
Sep. 30, 2016 (GB) ...................................... 1616647

(51) Int. Cl.
| | | |
|---|---|---|
| A61K 8/34 | (2006.01) | |
| A61Q 5/04 | (2006.01) | |
| A61K 8/33 | (2006.01) | |
| A61Q 5/00 | (2006.01) | |
| A61Q 5/12 | (2006.01) | |
| C07C 47/19 | (2006.01) | |

(52) U.S. Cl.
CPC ................ *A61K 8/342* (2013.01); *A61K 8/33* (2013.01); *A61Q 5/00* (2013.01); *A61Q 5/004* (2013.01); *A61Q 5/04* (2013.01); *A61Q 5/12* (2013.01); *C07C 47/19* (2013.01)

(58) Field of Classification Search
CPC ..................................................... A61Q 5/00
See application file for complete search history.

(56) References Cited

U.S. PATENT DOCUMENTS

| | | | |
|---|---|---|---|
| 2,683,175 A | 7/1954 | Himel et al. | |
| 3,665,072 A | 5/1972 | Kalopissis et al. | |
| 4,275,243 A | 6/1981 | Saito et al. | |
| 4,275,273 A | 6/1981 | Ts'Ao | |
| 4,932,977 A | 6/1990 | Schultz | |
| 5,302,378 A | 4/1994 | Crotty et al. | |
| 6,107,352 A * | 8/2000 | Zofchak | A61Q 19/00 516/914 |
| 6,455,742 B1 | 9/2002 | Cortright et al. | |
| 7,598,213 B2 * | 10/2009 | Geary | A61K 8/463 510/136 |
| 7,678,156 B2 | 3/2010 | Gross et al. | |
| 10,799,440 B2 * | 10/2020 | Gough | A61Q 5/12 |
| 11,234,917 B2 * | 2/2022 | Dixon | D06P 3/148 |
| 11,253,452 B2 * | 2/2022 | Dixon | A61Q 5/004 |
| 11,304,884 B2 * | 4/2022 | Gough | A61Q 5/04 |
| 11,311,471 B2 * | 4/2022 | Dixon | D06M 13/342 |
| 2008/0104772 A1 | 5/2008 | Gross et al. | |
| 2009/0126756 A1 | 5/2009 | Syed et al. | |
| 2009/0165812 A1 | 7/2009 | Resnick et al. | |
| 2010/0278767 A1 | 11/2010 | Hoffkes et al. | |
| 2015/0034117 A1 | 2/2015 | Pressly et al. | |
| 2015/0034119 A1 | 2/2015 | Pressly et al. | |
| 2015/0174028 A1 | 6/2015 | Washington et al. | |

FOREIGN PATENT DOCUMENTS

| | | | |
|---|---|---|---|
| CN | 1148340 C | 5/2004 | |
| FR | 2937543 A1 * | 4/2010 | ........... A61K 8/4913 |
| FR | 2937543 A1 | 4/2010 | |
| GB | 2075560 A | 11/1981 | |
| GB | 2552571 A | 1/2018 | |
| GB | 2552589 A | 1/2018 | |
| JP | 11199448 A | 7/1999 | |
| JP | 2001055672 A | 2/2001 | |
| JP | 2007191475 A | 8/2007 | |
| KR | 20070121282 A | 12/2007 | |
| RU | 2018137927 A | 5/2020 | |
| RU | 2018138297 A | 5/2020 | |
| WO | 2002003937 A2 | 1/2002 | |
| WO | 2016078970 A2 | 1/2002 | |
| WO | 2002030373 A2 | 4/2002 | |
| WO | 2003090700 A1 | 11/2003 | |

(Continued)

OTHER PUBLICATIONS

United Kingdom Combined Search and Examination Report dated Nov. 9, 2017, for application No. GB 1706356.1.
Donald Craig, et al. Additive Pummerer reactions of vinylic sulphoxides. Synthesis of γ-hydroxy-α,β-unsaturated esters and α-hydroxyketones, Thetrahedron Letters, vol. 31, No. 4, 1990, pp. 6441-6444.
Anita Mlakar, et al. Reinvestigation of lipid peroxidation of linolenic acid, Biochemica et Biophysica Acta, vol. 1214, 1994, pp. 209-220.
International Preliminary Report on Patentability dated Nov. 1, 2018, for international No. PCT/GB2017/05112.
International Search Report and Written Opinion dated Jul. 3, 2017, for international application No. PCT/GB2017/051112 international filing date Apr. 21, 2017.

(Continued)

*Primary Examiner* — Gina C Justice
(74) *Attorney, Agent, or Firm* — Carlos A. Fisher; Stout, Uxa & Buyan, LLP

(57) ABSTRACT

A method of treating a material, the method comprising contacting the material with a composition comprising a hydroxy-substituted aldehyde. In preferred aspects of the invention the material is a keratinous material.

20 Claims, No Drawings

(56) References Cited

FOREIGN PATENT DOCUMENTS

| WO | 2006060569 A2 | 6/2006 |
|---|---|---|
| WO | 2011027077 A2 | 3/2011 |
| WO | 2015074971 A1 | 5/2015 |
| WO | WO2015/074971 A1 | 5/2015 |
| WO | 2016078970 A1 | 5/2016 |
| WO | 2017182819 A1 | 10/2017 |
| WO | 2017182821 A1 | 10/2017 |
| WO | 2017182822 A1 | 10/2017 |
| WO | 2018060719 A1 | 5/2018 |
| WO | 2018060720 A1 | 5/2018 |

OTHER PUBLICATIONS

United Kingdom Search Report under section 17(5) dated Feb. 8, 2017, for application No. GB1607043.5.
Russian Office Action dated Jun. 25, 2020. (English translation).
Russian Office Action dated Nov. 11, 2020. (English translation).

\* cited by examiner

METHODS, COMPOSITIONS AND USES RELATING THERETO

CROSS-REFERENCE TO RELATED APPLICATIONS

This is a divisional of U.S. patent application Ser. No. 16/095,567, filed Oct. 22, 2018 as a U.S. National Stage application under 35 USC § 371 of International Patent Application PCT/GB2017/051112, filed Apr. 21, 2017 and claiming the benefit of each of British Patent Application GB 1607043.5, filed Apr. 22, 2016 and British Patent Application 1616647.2 filed Sep. 30, 2016. Each of these patent applications is hereby incorporated by reference herein in its entirety.

BACKGROUND AND SUMMARY

The present invention relates to a method of treating a material, to compositions for use in such methods and to uses relating thereto. In particular the present invention relates to a method of treating a keratinous material, especially hair, to provide a benefit to the material.

The appearance, condition and cleanliness of their hair is of great significance to many people. As a result, there is a vast array of hair care products available offering a wide range of benefits and containing a huge number of different components. However popular hair styles change continually with fashion trends and technological developments in hair styling appliances means that there is a continuing need for different and improved hair care compositions. Furthermore, as we learn more about the toxicity of certain chemicals and their environmental impact there is an increasing requirement to take these considerations into account when developing cosmetic products.

For example, one previously used constituent of cosmetic hair care compositions is formaldehyde. However, formaldehyde is a suspected carcinogen and thus its use in cosmetic compositions is now strictly regulated and highly undesirable.

The appearance, condition and cleanliness of textiles and fabric materials is also of considerable importance and the stresses encountered by these materials in the environments in which they are used may have a deleterious effect on them.

It is an aim of the present invention to provide means for enhancing at least one property of a material.

DETAILED DESCRIPTION OF THE INVENTION

According to a first aspect of the present invention there is provided a method of treating a material, the method comprising contacting the material with a composition comprising a hydroxy-substituted aldehyde.

The present invention relates to a method of treating a material. In some embodiments the material may be textile material. In such embodiments the textile material suitably comprises wool and preferably comprises wool as a major proportion thereof.

In preferred embodiments the material is a keratinous material. More preferably the material comprises keratinous fibres. Preferably the material is hair. The hair may be human or animal hair. In especially preferred embodiments the method of the present invention is a method treating human hair. Most preferably it is a method of treating human hair growing on the head.

However, it will be appreciated that the method of the present invention can also be used to treat from hair that is not growing on the head, such as a wig or animal hair, for example wool.

The method of the present invention involves contacting the material, preferably hair, with a composition comprising a hydroxy-substituted aldehyde.

According to a second aspect of the present invention there is provided a composition comprising a hydroxy-substituted aldehyde.

In preferred embodiments the method of the first aspect of the present invention involves contacting the material with the composition of the second aspect. Thus, preferred features of the second aspect apply equally to the first aspect.

Preferred features of the first and second aspects of the invention will now be described. Any feature may apply to any other aspect as appropriate.

The composition of the second aspect of the present invention comprises a hydroxy-substituted aldehyde.

Any suitably hydroxy-substituted aldehyde may be included.

Suitable aldehydes for use herein have at least 2 carbon atoms. Preferably they have at least 3 carbon atoms.

Suitable aldehydes for use herein may have up to 36 carbon atoms, preferably up to 30 carbon atoms, more preferably up to 24 carbon atoms, preferably up to 20 carbon atoms, for example up to 18 carbon atoms or up to 16 carbon atoms.

Some preferred aldehydes for use herein have from 3 to 20 carbon atoms, for example 3 to 16 carbon atoms.

Same preferred aldehydes for use herein have from 3 to 12 carbon atoms, for example 3 to 11 carbon atoms.

Some especially preferred aldehydes for use herein have from 3 to 9 carbon atoms, more preferably from 3 to 8 carbon atoms.

Some other preferred aldehydes for use herein have from 8 to 16 carbon atoms, for example 10 to 14 carbon atoms.

The aldehyde may comprise one or more hydroxy substituents.

Suitably the aldehyde comprises one, two or three hydroxy substituents, preferably one or two substituents.

In some preferred embodiments the aldehyde is not a saccharide.

Preferably the aldehyde comprises one hydroxy substituent.

Suitably the aldehyde has a hydroxy substituent at the 2, 3 or 4 position.

In some embodiments the aldehyde may have a hydroxy substituent at the 2 and 3 or the 2 and 4 positions.

Suitably the aldehyde may have a hydroxy substituent at the 2 position and/or the 3 position.

Suitably the aldehyde may have a hydroxy substituent at the 2 position or the 3 position.

In especially preferred embodiments the aldehyde has a hydroxy substituent at the 2 position. Thus, the aldehyde is suitably an α-hydroxy aldehyde/a 2-hydroxy aldehyde.

The aldehyde has a hydroxy substituent. It may have one or more further substituents.

Suitable further substituents may be selected from a further hydroxy substituent, a further aldehyde group, a keto group, a carboxy group, an acyl group, a halo group, an alkoxy group, an alkyl group, a nitro group, an amino group, a sulfoxy group, a mercapto group, an amide, an ester, a nitrile group or an isonitrile group.

Preferred halo substituents are chloro, fluoro, and bromo.

Preferred alkoxy substituents are methoxy, ethoxy, propoxy and butoxy, including isomers thereof.

Preferred alkyl substituents are $C_1$ to $C_8$ alkyl, preferably $C_1$ to $C_6$ alkyl, including isomers thereof.

In some embodiments the hydroxyaldehyde may include a further aldehyde functional group. Suitably such further aldehyde groups may be α-substituted.

In preferred embodiments the aldehyde includes a hydrocarbon chain. This is suitably a chain with a carbon backbone. However, compounds in which the carbon backbone is interrupted by one or more heteroatoms are also within the scope of the invention. For example, the carbon backbone may be interrupted by one or more oxygen, sulfur or nitrogen molecules and thus the aldehyde may include an ether, a thioether, an amine or a disulfide moiety.

The aldehyde may be predominantly aliphatic or predominantly aromatic in nature. Preferably the aldehyde is aliphatic. However, it may include one or more double bonds and/or one or more cyclic groups. It may be straight-chain or branched.

In some especially preferred embodiments the aldehyde has the formula (I):

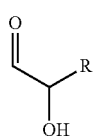

(I)

wherein R is hydrogen or an optionally substituted hydrocarbyl group having 1 to 30 carbon atoms.

R may be hydrogen or an optionally substituted alkyl, alkenyl or aryl group having 1 to 30 carbon atoms, preferably 1 to 20 carbon atoms, more preferably 1 to 10 carbon atoms.

Preferably R is hydrogen or an optionally substituted alkyl or alkenyl group having 1 to 30, preferably 1 to 20, suitably 1 to 10 carbon atoms.

In some embodiments R is an optionally substituted alkyl or alkenyl group having 1 to 7, preferably 1 to 6 carbon atoms.

In some embodiments R is an optionally substituted alkyl or alkenyl group having 8 to 14, preferably 8 to 12 carbon atoms.

R may be substituted with one or more substituents selected from keto, hydroxy, halo, carboxy, acyl, nitro, amino, mercapto, alkoxy, sulfoxy, ester, nitrile, isonitrile or amide. The carbon backbone may be interrupted by one or more heteroatoms, for example one or more oxygen, nitrogen or sulfur atoms.

In some preferred embodiments R is an unsubstituted alkyl group having 1 to 8, preferably 1 to 6 carbon atoms.

In preferred embodiments R is an unsubstituted alkyl group having 4 to 16, preferably 8 to 12 carbon atoms.

R may be selected from hydroxy methylene, methyl, butyl, hexyl, octyl, decyl and dodecyl. These groups may be straight-chained or branched. Preferably they are straight-chained.

Suitably R is selected from hydroxy methylene, methyl, n-butyl and n-hexyl.

R may be selected from methyl, n-butyl, n-hexyl n-octyl, n-decyl and n-dodecyl.

Preferably R is selected from methyl, n-butyl and n-hexyl.

Most preferably R is selected from n-butyl and n-hexyl.

In some preferred embodiments the aldehyde is a hydroxy-substituted aliphatic aldehyde.

Suitable hydroxy-substituted aldehydes for use herein include 2-hydroxydecanal, 2-hydroxydodecanal, 2-hydroxytetradecanal, 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Suitable hydroxy-substituted aldehydes for use herein include 2-hydroxydecanal, 2-hydroxydodecanal, 2-hydroxytetradecanal, 2-hydroxyhexanal, 2-hydroxyoctanal, 2-hydroxypropanal, 6-hydroxyhexanal, 3-hydroxypropanal, 4-hydroxy-but-2-enal, 2-hydroxybutanal, 3-hydroxybutanal and 4-hydroxybutanal.

Preferred hydroxy-substituted aldehydes for use herein include 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

Preferred hydroxy-substituted aldehydes for use herein include 2-hydroxyhexanal, 2-hydroxyoctanal, 2-hydroxypropanal, 6-hydroxyhexanal, 3-hydroxypropanal, 4-hydroxy-but-2-enal, 2-hydroxybutanal, 3-hydroxybutanal and 4-hydroxybutanal.

More preferred hydroxy-substituted aldehydes for use herein include 2-hydroxyhexanal, 2-hydroxyoctanal, 2-hydroxypropanal and glyceraldehyde.

Most preferred hydroxy-substituted aldehydes for use herein are 2-hydroxyhexanal and 2-hydroxyoctanal and 2-hydroxypropanal.

More preferred hydroxy-substituted aldehydes for use herein include 2-hydroxyhexanal, 2-hydroxyoctanal, 2-hydroxypropanal and glyceraldehyde.

Most preferred hydroxy-substituted aldehydes for use herein are 2-hydroxyhexanal and 2-hydroxyoctanal and 2-hydroxypropanal.

Suitably the composition comprises a hydroxy-substituted aldehyde in the amount of at least 0.1 wt %, suitably at least 0.5 wt %, preferably at least 1 wt %, for example at least 1.5 wt %.

The composition may comprise a hydroxy-substituted aldehyde in the amount of up to 50 wt %, preferably up to 30 wt %, suitably up to 20 wt %, preferably up to 10 wt %, more preferably up to 5 wt %, for example up to 4 wt %, up to 3 wt % or up to 2.75 wt %.

In some embodiments the composition comprises from 0.1 to 10 wt % of hydroxyaldehyde, preferably from 0.5 to 5 wt %, suitably from 0.5 to 3 wt %.

In some alternative embodiments the composition may comprise much greater concentrations of hydroxyaldehyde, for example from 20 to 100 wt %, preferably from 50 to 100 wt %, for example from 70 to 100 wt % or from 90 to 100 wt %.

The composition of the second aspect may comprise a mixture of two or more hydroxy-substituted aldehydes. In such embodiments the above amounts refer to the total amount of all such compounds present in the composition.

In some embodiments the composition of the second aspect comprises a mixture of two or more hydroxy-substituted aldehydes.

In some embodiments the composition of the second aspect comprises 2-hydroxyoctanal and one or more further hydroxy-substituted aldehydes.

In some embodiments the composition of the second aspect comprises glyceraldehyde and one or more further hydroxy-substituted aldehydes.

In some embodiments the composition of the second aspect comprises 2-hydroxyoctanal and glyceraldehyde. It may optionally comprise one or more further hydroxy-substituted aldehydes.

In some embodiments the composition comprises less than 0.1 wt % glyceraldehyde, suitably less than 0.01 wt %. Suitably the composition does not comprise glyceraldehyde.

In some embodiments the composition of the third aspect comprises a first hydroxy-substituted aldehyde having less than 10 carbon atoms and a second hydroxy-substituted aldehyde having 10 or more carbon atoms. It may optionally comprise one or more further hydroxy-substituted aldehydes. For example, the composition of the third aspect may comprises a first hydroxy-substituted aldehyde having 3 to 9 carbon atoms, preferably 3 to 8 carbon atoms and a second hydroxy-substituted aldehyde having 10 to 18 carbon atoms, preferably 10 to 16 carbon atoms, more preferably 10 to 14 carbon atoms. It may optionally comprise one or more further hydroxy-substituted aldehydes.

In some embodiments the composition of the third aspect comprises one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal, 2-hydroxypropanal, glyceraldehyde, 6-hydroxyhexanal, 3-hydroxypropanal, 4-hydroxy-but-2-enal, 2-hydroxybutanal, 3-hydroxybutanal and 4-hydroxybutanal.

In some embodiments the composition of the third aspect comprises one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal, 2-hydroxypropanal, 6-hydroxyhexanal, 3-hydroxypropanal, 4-hydroxy-but-2-enal, 2-hydroxybutanal, 3-hydroxybutanal and 4-hydroxybutanal.

In some embodiments the composition of the third aspect may comprise one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal, 2-hydroxypropanal and glyceraldehyde.

In some embodiments the composition of the third aspect may comprise one or more hydroxy-substituted aldehydes selected from 2-hydroxydecanal, 2-hydroxydodecanal and 2-hydroxytetradecanal and one or more further hydroxy-substituted aldehydes selected from 2-hydroxyhexanal, 2-hydroxyoctanal and 2-hydroxypropanal.

The composition of the present invention may be provided in any suitable form. It may be in the form of a gel, paste, cream or wax. It may be in the form of a liquid composition. Such compositions may be in the form of a solution, dispersion or emulsion. It may be provided as a solid composition, for example as a powder or as a bar. In some embodiments a concentrate composition to be diluted prior to use may be provided. In some embodiments the composition of the second aspect may be part of precursor composition to be mixed with one or more further components prior to contact with the material.

The form and nature of the composition of the second aspect will depend on the intended use thereof.

In some embodiments the composition is a laundry detergent composition. In such embodiments the composition suitably comprises one or more further ingredients selected from builders, surfactants, chelating agents, bleaches, optical brighteners, enzymes, fragrances and other such ingredients commonly found in laundry detergent compositions.

The composition may be a hand washing laundry detergent composition or an automatic laundry detergent composition.

In especially preferred embodiments the composition is a hair care composition.

The method of the first aspect of the present invention preferably provides a benefit to the material treated. Suitably the method enhances at least one property of the material that is treated according to the method.

In preferred embodiments the method is a method of treating hair that provides a beneficial effect to the hair. Suitably it enhances at least one property of the hair. Suitably the method of the first aspect involves contacting the hair with a composition of the second aspect.

The composition of the second aspect of the present invention is preferably a hair benefit composition. Suitably it enhances at least one property of the hair.

In some embodiments the composition and method of the present invention may provide a temporary change to a property of the hair, for example by providing increased shine or gloss, or improved softness or combability.

A temporary change in the property of the hair may be due to the composition coating the surface of the hair but forming a weak interaction such that the composition can be easily washed or brushed away.

In some preferred embodiments the composition and method of the present invention may provide a longer lasting benefit to the hair, for example a wash-durable benefit.

A longer lasting benefit to the hair may be achieved due to interaction of the hydroxyaldehyde molecules with the hair. Without wishing to be bound by theory it is believed that the aldehyde forms a Schiff base with amino groups in the keratin fibres of the hair. The Schiff base can then either go on to react with further amino groups in the hair to form covalent cross links thereby giving permanency to the particular hair benefit, and/or the alkyl or aryl etc groups which are part of the hydroxy-substituted aldehyde compound bound as a Schiff base to amino groups in the hair form hydrophobic bonds with each other to give permanency to the particular hair benefit. This mechanism could apply to all of the benefits covered in this invention such as hair waving, hair straightening, hair strengthening, hair protein retention, binding extra protein to the hair, thermal durability, chemical resistance, UV stability, shine, softness and combability. To afford these benefits, it will be appreciated that the hydroxy-substituted aldehyde compounds will operate either by fully or partially penetrating to the core of the hair (cortex) and reacting with amino groups partially or throughout the hair fibre, and/or reacting with amino groups that are on/near the surface of the hair. In the latter case, the alkyl/aryl etc groups of the hydroxy-substituted aldehyde compound will be covalently bound to the surface of the hair fibre to afford benefits such as shine/gloss, protection, softness and combability.

The composition and method of the present invention may be useful in permanent waving or straightening of the hair.

The composition and method of the present invention may improve the strength of the hair.

The composition and method of the present invention may prevent or inhibit loss of protein from the hair and/or they may be used to bind extra protein to the hair.

The composition and method of the present invention may provide protection to the hair against damage. For example, the composition and method of the present invention may protect against damage from heat or sunlight.

In some embodiments the composition and method of the present invention may provide chemical resistance, for example protection against chlorine and other compounds found in swimming pools and the like.

Suitably the composition and method of the present invention may enhance at least one property of hair selected from shine, gloss, softness, combability, strength, straightness, waviness, thermal durability and UV stability.

Preferably the invention provides one or more benefits selected from increased and/or permanent/semi-permanent gloss or shine, improved and/or permanent/semi-permanent combability, improved and/or permanent/semi-permanent strength, increased and/or permanent/semi-permanent softness, reduced protein loss, improved thermal durability, increased chemical resistance, permanent/semi-permanent waviness and and/or permanent/semi-permanent straightness.

Suitably the composition comprises one or more diluents or carriers. Preferred diluents and carriers are cosmetically approved compounds and suitable examples of these will be known to the person skilled in the art. Examples of suitable carriers include organic solvents (eg, hydrocarbon solvents (eg, isododecane), alcohols (eg, ethanol, propanol and butanol), propylene carbonate, benzyl alcohol, aliphatic or aromatic esters (eg, vegetable oils, isopropyl myristate, C12-15 alkyl benzoate), perfluorocarbon solvents, and silicone fluids.

In some embodiments the composition is an aqueous composition. Suitably water is the major solvent present in the composition. In some embodiments water provides for at least 50 wt % of all solvents present in the composition, preferably at least 60 wt %, more preferably at least 70 wt %, suitably at least 80 wt %, for example at least 90 wt % or at least 95 wt %. In some embodiments one or more further water miscible solvents may be present. Examples of suitable water miscible solvents include monohydric and polyhydric alcohols, for example ethanol, glycerol and isopropanol.

In some embodiments the composition of the present invention is not aqueous, and the major diluent or carrier is an oleophilic material. In such embodiments the composition may comprise as a major solvent one or more higher fatty alcohols, a mineral oil and/or a vegetable oil.

In some embodiments the composition is substantially aqueous, but the aldehyde is dispersed within an oleophilic phase in which it is soluble.

In some embodiments the composition may consist essentially of one or more hydroxy-substituted aldehydes and one or more diluents or carriers. In preferred embodiments the composition comprises one or more further components. Suitable components are those typically used in personal care compositions and are known to the person skilled in the art.

As detailed above the compositions of the present invention may comprise different components depending on the intended use thereof. In some embodiments the composition may be used immediately after dyeing the hair. Alternatively, the composition may be used one or more times as a hair treatment composition. In some embodiments it may be provided as a colour-loss prevention composition. Alternatively, the composition may be in the form of shampoo, conditioner or hair styling product, for example a serum, wax, mousse, gel or spray or any other hair treatment form that could be used to provide general hair care benefits. Compositions which perform multiple functions, for example combined shampoo and conditioning compositions are also within the scope of the invention.

Suitably the composition comprises one or more additional components selected from surfactants (including anionic, amphoteric, nonionic and cationic surfactants); conditioning agents (including quaternary ammonium compounds, cationic polymers, silicones, synthetic or natural oils or resins etc), fatty alcohols, electrolytes or other rheology modifiers, opacifying/pearlising agents, scalp benefit agents, fragrances, dyes, UV filters, penetration enhancers (eg, propylene carbonate, benzyl alcohol etc), preservatives, antioxidants, emulsifiers, pH adjusting agents and buffers and styling polymers (eg, polyvinylpyrrolidone etc).

In some embodiments the composition comprises a pH adjusting agent.

Suitable pH adjusting agents for use herein may include lactic acid, sodium hydroxide, sodium phosphate and salts and buffers thereof.

The pH of the composition will depend on the intended use thereof. However, in preferred embodiments the composition has a pH of between 3 and 9, preferably between 3.5 and 8, more preferably between 4 and 7, preferably between 4 and 6.

In some preferred embodiments the composition is a hair care composition. Suitable hair care compositions include shampoo compositions, conditioning compositions, hair styling compositions and hair permanent waving, relaxing or permanent straightening compositions, or hair colouring compositions.

Suitable further ingredients and amounts thereof to be used in hair care compositions will be known to the person skilled in the art. The relative ratios of the components and the formulation of such compositions would be within the competence of the skilled person.

Suitably the composition is a substantially aqueous composition, suitably comprising at least 50 wt % water, preferably at least 60 wt %, more preferably at least 70 wt %.

Suitably the composition comprises one or more surfactants. For example, the composition may comprise from 0.1 to 60 wt % surfactants, preferably 1 to 30 wt %, suitably from 5 to 25 wt %.

Suitably the composition comprises one or more anionic surfactants. For example, the composition may comprise from 0.1 to 60 wt % anionic surfactants, preferably 1 to 30 wt %, suitably from 5 to 25 wt %.

In some embodiments the composition may comprise a quaternary ammonium salt, suitably in an amount of from 0.1 to 20 wt %, preferably 0.1 to 10 wt %.

In some embodiments the composition further comprises a succinimidyl ester. Suitable compounds of this type are described in FR2937543.

Thus, the present invention may provide a hair care composition comprising a hydroxy-substituted aldehyde and a succinimidyl ester.

In such embodiments the aldehyde is suitably present in an amount of from 0.1 to 50 wt %, preferably 0.1 to 10 wt %, more preferably 0.5 to 5 wt % and the succinimidyl ester is suitably present in an amount of from 0.1 to 50 wt %, preferably 0.1 to 10 wt %, more preferably 0.5 to 5 wt %.

Preferably the succinimidyl ester is a compound of formula (I):

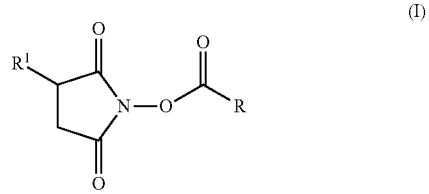

wherein R is an optionally substituted hydrocarbyl group having 5 to 36 carbon atoms; and $R^1$ is hydrogen or a solubilising group.

Preferably R is an optionally substituted alkyl, alkenyl or aryl group having 5 to 20 carbon atoms. More preferably R is selected from phenyl and $CH_3(CH_2)_n$ wherein n is 4 to 10.

Suitably $R^1$ is hydrogen or a sulfonate moiety, preferably hydrogen.

In some embodiments the composition further comprises a chelating agent. Preferred chelating agents are polycarboxylic acid-derived chelating agents.

Thus, the present invention may provide a hair care composition comprising a hydroxy-substituted aldehyde and a polycarboxylic acid-derived chelating agent.

In such embodiments the aldehyde is suitably present in an amount of from 0.1 to 50 wt %, preferably 0.1 to 10 wt %, more preferably 0.5 to 5 wt % and the chelating agent is suitably present in an amount of from 0.1 to 50 wt %, preferably 0.1 to 10 wt %, more preferably 0.5 to 5 wt %.

Suitably the chelating agent is selected from glutamic acid N,N-diacetic acid (GLDA), diethylene triamine pentaacetic acid (DTPA), imido disuccinic acid (IDS), ethylene diamine tetraacetic acid (EDTA), ethylene diamine disuccinic acid (EDDS), hydroxyethyl ethylenediaminetriacetic acid (HEDTA), citric acid and mixtures thereof.

In some preferred embodiments the chelating agent is selected from DTPA, GLDA, IDS and mixtures thereof. In some especially preferred embodiments the chelating agent is selected from DTPA, GLDA and mixtures thereof.

In some embodiments the composition further comprises an amine salt of a carboxylic acid. Preferred compounds of this type are amine salts of a carboxylic acid wherein the carboxylic acid has 4 to 10 carbon atoms.

Preferably the salt is of a secondary or tertiary alkylamine and/or alkanolamine or a substituted alkylene diamine. Triethanolamine and diethanolamine are especially preferred.

Most preferably the salt is the triethanolamine or diethanolamine salt of n-hexanoic acid or n-octanoic acid.

In some embodiments the composition further comprises an amine salt of a carboxylic acid and a polycarboxylic acid derived chelating agent.

In some embodiments the composition further comprises an amine salt of a carboxylic acid, and a succinimidyl ester.

In some embodiments the composition further comprises a succinimidyl ester and a polycarboxylic acid derived chelating agent.

In some embodiments the composition further comprises an amine salt of a carboxylic acid, a succinimidyl ester and a polycarboxylic acid derived chelating agent.

In some embodiments the composition may further comprise a crosslinking agent comprising two or more reactive moieties and a linker. Compounds of this type are described for example in US2015/034117 and US2015/0034119.

In some embodiments the reactive moieties are activated carboxylic acid or sulfonic acid derivatives and the linkers are polyamino compounds which may form salts or covalent bonds with the reactive moieties.

In some embodiments the reactive moieties are maleic acid derivatives and the linker has two or more amino groups linked by alkylene or oxyalkylene chains. The crosslinking agent may be a maleimide or a maleic acid amine salt.

In some embodiments the reactive moieties are maleic acid ions and the linker comprises quaternary ammonium ions linked by alkylene or oxyalkylene chains.

Some preferred crosslinking agents have the following structures:

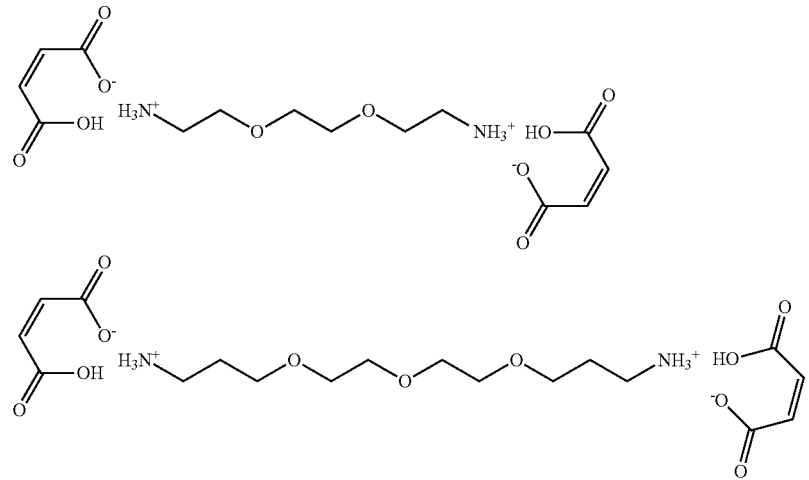

Thus, the present invention may provide a hair care composition comprising a hydroxy-substituted aldehyde and an amine salt of a carboxylic acid.

In such embodiments the aldehyde is suitably present in an amount of from 0.1 to 50 wt %, preferably 0.1 to 10 wt %, more preferably 0.5 to 5 wt % and the amine salt is suitably present in an amount of from 0.1 to 50 wt %, preferably 0.1 to 10 wt %, more preferably 0.5 to 5 wt %.

Suitably the carboxylic acid has 4 to 10 carbon atoms, preferably 6 to 8 carbon atoms.

The crosslinking agent comprising two or more reactive moieties and a linker may be present in an amount of from 0.1 to 30 wt %, preferably 0.1 to 10 wt %, suitably 0.5 to 5 wt %.

In some embodiments the composition of the second aspect of the present invention is a shampoo composition.

Suitable shampoo compositions of the present invention may typically comprise 0.5 to 60 wt % of one or more anionic surfactants, preferably 1 to 50 wt %, more preferably 5 to 30 wt %, for example 8 to 20 wt % or 8 to 12 wt %; optionally from 0.1 to 30 wt % of amphoteric surfactants, preferably 1 to 15 wt %, for example 2 to 12 wt %; and optionally 0.1 to 40 wt % of non-ionic surfactants, preferably 0.5 to 30 wt %, for example 1 to 15 wt % or 2 to 12 wt %.

Shampoo compositions of the present invention may comprise one or more ingredients selected from anionic surfactants (eg, sodium laureth sulfate, sodium lauroyl methyl isethionate, sodium cocoyl methyl isethionate, sodium alpha-olefin sulfonate, sodium lauryl sulfoacetate, sodium monoalkyl phosphates, sodium dialkyl phosphates and sodium methyl cocoyl taurate), amphoteric surfactants (eg, cocamidopropyl betaine, sodium lauroamphoacetate, cocamidopropylhydroxy sultaine and disodium cocoamphodiacetate), foam boosters (eg, cocamide DEA, cocamide MEA, cocamide MIPA laureth-3), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), rheology modifiers (eg, carbomer, PEG-150 distearate and xanthan gum), synthetic or natural oils or resins (eg, mineral oil or vegetable oils), anti-dandruff agents (eg, piroctone olamine, zinc pyrithione and salicylic acid), styling agents (eg, polyisobutylene and polyvinyl pyrollidone/vinyl acetate copolymer), moisturising agents (eg, panthenol and glycerol), non-polymeric conditioning agents (eg, quaternary ammonium compounds such as behentrimonium chloride and stearalkonium chloride), opacifying/pearlising agents (eg, styrene/acrylates copolymer and ethylene glycol distearate), scalp benefit agents, fragrances, colouring agents, hair dyes, sunscreens, UV filters, preservatives, penetration enhancers (eg, propylene carbonate, benzyl alcohol etc) and diluents and carriers as defined herein.

Some preferred shampoo compositions of the present invention include 0.5 to 60 wt % of one or more anionic surfactants (for example, sodium laureth sulfate, sodium lauroyl methyl isethionate, sodium cocoyl isethionate, sodium alpha-olefin sulfonate, sodium lauryl sulfoacetate, sodium monoalkyl phosphates and sodium dialkyl phosphates); and 0 to 30 wt % of amphoteric surfactants (for example, cocamidopropyl betaine, sodium lauroamphoacetate and cocamidopropylhydroxy sultaine).

In some embodiments the composition of the second aspect of the present invention is a conditioning composition.

Suitable conditioning compositions of the present invention may typically comprise 0.1 to 20 wt % of one or more cationic surfactants, preferably 0.5 to 8 wt %, more preferably 1 to 4 wt %; and 0.1 to 20 wt % of one or more fatty alkyl alcohols, preferably 0.5 to 8 wt %, more preferably 1 to 4 wt %; and optionally 0.1 to 20 wt % of one or more non-ionic surfactants, preferably 0.5 to 8 wt %, more preferably 1 to 4 wt %; and optionally 0.1 to 20 wt % of one or more cationic polymers, preferably 0.5 to 8 wt %, more preferably 1 to 4 wt %.

Conditioning compositions of the present invention including rinse-off and leave-on conditioners (including 'hair masks') and hair shine or appearance enhancing products, anti-frizz treatment serums and other treatments, either leave-in or rinse-off, designed to be applied to the hair immediately after colouring or any time thereafter, and hair-tonics. Such compositions may comprise one or more further ingredients selected from: cationic surfactants including mono- and di-fatty alkyl tertiary amines and quaternary ammonium compounds (eg, mono- and di-fatty alkyl quaternary ammonium compounds, such as cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates, eg, ceteareth-20), cationic polymers (eg, guar hydroxypropyl trimonium chloride, polyquaternium-10), silicones (eg, polydimethylsiloxanes such as dimethicone and dimethiconol), rheology modifiers (eg, hydroxyethyl cellulose and polyquaternium-37), moisturising agents (eg, panthenol and glycerol), non-polymeric conditioning agents (eg, quaternary ammonium compounds such as behentrimonium chloride and stearalkonium chloride), scalp benefit agents, fragrances, colouring agents, hair dyes, sunscreens, UV filters preservatives, penetration enhancers (eg, propylene carbonate, benzyl alcohol etc), and diluents and carriers as defined herein.

Some preferred conditioning compositions of the present invention include 0.1 to 20 wt % of cationic surfactants (for example mono- and di-fatty alkyl quaternary ammonium compounds, mono- and di-fatty alkyl tertiary amines), 0.1% to 20 wt % of fatty alkyl alcohols; and 0.1% to 20 wt % of non-ionic surfactants (for example ceteareth-20).

In some embodiments the composition of the second aspect of the invention is a hair styling composition.

Suitable hair styling compositions of the present invention may typically comprise from 0.1 to 40 wt % of one or more hair styling polymers, preferably from 0.1 to 30 wt %, more preferably from 0.5 to 10 wt %.

Hair styling compositions of the present invention (including gels, mousses with and without propellant, hair sprays with and without propellant, hair pomades, hair waxes, hair creams, hair brilliantines and compositions designed to be used in conjunction with heated styling appliances such as blow dryers, curling tongs, straightening irons, hot air hoods (as used for example in hair salons)) may comprise one or more further ingredients selected from: hair styling polymers (eg, polyvinylpyrrolidone, polyvinylpyrrolidone/vinyl acetate copolymers, octylacrylamide/acrylates/butylaminoethyl methacrylate copolymer, methyl vinyl ether/maleic anhydride copolymers and polyethylene waxes), rheology modifiers (eg, carbomers, acrylates copolymers, hydroxyethylcellulose, xanthan gum and polyquaternium-37), aminomethyl propanol, fatty alkyl alcohols (eg, cetyl alcohol, stearyl alcohol and behenyl alcohol), ethanol, propyl alcohol, isopropyl alcohol, petrolatum, mineral oil, ozokerite, beeswax, carnauba wax, silicones (eg, polydimethylsiloxanes such as dimethicone and dimethiconol), polyethylene glycols, anionic surfactants (eg, sodium laureth sulfate and sodium lauroyl methyl isethionate), amphoteric surfactants (eg, cocamidopropyl betaine and disodium cocoamphodiacetate), nonionic surfactants (eg, alkylpolyglucosides and alkyl ether ethoxylates), cationic polymers (eg, guar hydroxypropyl trimonium chloride, Polyquaternium-10), silicones (eg, polydimethylsiloxanes such as dimethicone and dimethiconol), moisturising agents (eg, panthenol and glycerol), non-polymeric conditioning agents (eg, quaternary ammonium compounds such as behentrimonium chloride and stearalkonium chloride), scalp benefit agents, fragrances, colouring agents, hair dyes, sunscreens, UV filters, preservatives, penetration enhancers (eg, propylene carbonate, benzyl alcohol etc), and diluents and carriers as defined herein.

Some preferred hair styling compositions of the present invention include 0.1 to 40 wt % of one or more hair styling polymers/resins (for example polyvinylpyrrolidone, polyvinylpyrrolidone/vinyl acetate copolymers, octylacrylamide/ acrylates/butylaminoethyl methacrylate copolymer, methyl vinyl ether/maleic anhydride copolymers and polyethylene waxes).

Those skilled in the art will appreciate that it is possible to confer one or more attributes of hair conditioning, shine etc, and hair styling to the hair from a single product containing the appropriate ingredients thus compositions having such combinations of hair benefit effects are also covered in the invention.

In some embodiments the composition of the second aspect is a hair permanent waving composition.

Suitable hair permanent waving compositions of the present invention may typically comprise 0.1 to 20 wt % of one or more reducing agents, preferably from 0.5 to 15 wt %, more preferably 3 to 12 wt %.

Some preferred hair permanent waving compositions of the present invention include 0.5 to 15 wt % of one or more reducing agents (for example as thioglycolic acid, ammonium thioglycolate, thiolactic acid, cysteamine, cysteine, glycerol monothioglycolate, sodium sulfite/bisulfite); alkalising agents (for example ammonia, monoethanolamine) in an amount sufficient to adjust the pH of the reducing component to between pH 8-13. Hair permanent waving compositions are typically provided in a package with a second composition comprising 0.5 to 10 wt % of one or more oxidising agents (for example hydrogen peroxide, sodium bromate, sodium percarbonate and sodium perborate) which are applied after the reducing agent composition has been applied, allowed to process and then rinsed off, In some embodiments the composition of the second aspect of the present invention is a hair relaxing composition.

Hair relaxing compositions of the present invention may include one or more ingredients selected from sodium hydroxide, lithium hydroxide, potassium hydroxide, calcium hydroxide and guanidine carbonate. These components are suitably present in an amount of from 0.5 to 5 wt %

Other types of permanent straightening compositions may include one or more ingredients selected from formaldehyde, glycoxylic acid, glutaraldehyde and glyoxyloyl carbocysteine. These components are suitably present in an amount of from 0.1 to 10 wt %

The hair permanent waving, relaxing and permanent straightening compositions mentioned above may further include one or more additional ingredients selected from anionic surfactants (eg, sodium laureth sulfate and sodium lauroyl methyl isethionate), amphoteric surfactants (eg, cocamidopropyl betaine and disodium cocoamphodiacetate), quaternary ammonium compounds (eg, cetrimonium chloride, steartrimonium chloride and behentrimonium chloride), fatty alkyl alcohols (eg, cetyl alcohol, stearyl alcohol and behenyl alcohol), nonionic surfactants (eg, alkylpolyglucosides and alkyl ether ethoxylates), cationic polymers (eg, guar hydroxypropyl trimonium chloride, polyquaternium-10), silicones (eg, polydimethylsiloxanes such as dimethicone and dimethiconol), opacifying agents (eg, styrene acrylates copolymer), rheology modifiers (eg, hydroxyethyl cellulose and xanthan gum), moisturising agents (eg, panthenol and glycerol), non-polymeric conditioning agents (eg, quaternary ammonium compounds such as behentrimonium chloride and stearalkonium chloride), fragrances, sunscreens, UV filters, colouring agents and diluents and carriers as defined herein.

In some embodiments the composition of the second aspect of the present invention is a hair colouring composition.

Hair colouring compositions may include a dye compound and/or may include a dye precursor compound which forms an active dye in the hair in situ following admixture with an oxidising composition.

Oxidative hair colouring compositions of the present invention may include one or more intermediates, for example p-phenylenediamine, N,N-bis(2-hydroxyethyl)-p-phenylenediamine, p-toluenediamine, p-aminophenol phenyl methyl pyrazolone, m-phenylenediamine, resorcinol, 1-naphthol, 1-hydroxyethyl 4,5-diamino pyrazole and m-aminophenol. These intermediates can be present in any combination and ratios at a total intermediate concentration of from 0.01% to 15%, depending upon the desired shade. Such compositions typically further include one or more alkalising agents, for example ammonia, ammonium hydroxide, sodium hydroxide and monoethanolamine. Developer compositions for oxidative dyeing include an oxidising agent, for example hydrogen peroxide, sodium bromate, sodium percarbonate or sodium perborate. These are typically present in an amount of from 0.1 to 30 wt %.

Direct-dye colour compositions of the present invention may include one of more direct dyes for example from the classes of nitrophenylenediamines (eg, 4-nitro-o-phenylenediamine etc), nitroaminophenols (eg, 2-amino-4-nitrophenol etc) and aminoanthraquinones (eg, Disperse Red 11 etc). These are typically present in an amount of 0.1 wt % to 20 wt %, depending on the desired shade.

In some preferred embodiments the composition of the present invention is not a hair colouring composition. Preferably the composition comprises less than 0.1 wt %, preferably less than 0.01 wt % of dye compounds and/or dye precursor compounds. Preferably the composition does not comprise dye compounds and/or dye precursor compounds. Compounds which provide colour to the composition such as pigments and pearlescent agents may be present but suitably the composition does not include any compounds which may be used to dye hair.

In the method of the first aspect the material is contacted with a composition comprising a hydroxy-substituted aldehyde.

The material, preferably hair, may be wet or dry when contacted with the composition.

Suitably the composition is applied to the material and spread across the surface of the material. In preferred embodiments in which the material is hair the composition may be rubbed into the hair in the manner of a shampoo and/or it may be combed through the hair.

The composition of the present invention may be left on the material or it may be removed from the material. Suitably it may be rinsed using warm water.

In some embodiments the composition may be contacted with the material, spread throughout and then immediately removed.

Suitably the composition may be removed from the material by rinsing, preferably by using water.

In some embodiments the composition may be washed from the material by washing with a detergent composition.

In some embodiments the composition may be mechanically removed from the material, for example by brushing.

In some embodiments the composition may be left on the material and not removed until the material is washed during a normal cycle.

In some embodiments in which the material is hair, the composition may be applied to the hair, spread throughout and rubbed into the hair, and then rinsed with water, in the manner of a shampoo.

In some embodiments in which the material is hair, the composition may be applied to the hair, spread throughout the hair (optionally with combing), left on the hair for a short period and then rinsed from the hair with water, in the manner of a conditioner.

In some embodiments in which the material is hair, the composition may be contacted with the hair and left on the hair in the manner of a styling product. The composition may be sprayed throughout the hair, rubbed throughout the hair, combed throughout the hair or otherwise spread through the hair in a manner known to those skilled in the art.

In embodiments in which the composition is left on the hair, it suitably remains on the hair until the hair is next washed, although some of the composition may be brushed out or rubbed away during normal activity.

In the method of the present invention the composition is suitably contacted with the material, preferably hair, at ambient temperature. In some embodiments the composition may be contacted with the material at a temperature greater than the ambient temperature.

In some embodiments the composition may be contacted with the hair and the hair carrying the compositions is then heated and/or manipulated and/or dried. Thus the hair may be dried using a hairdryer or straightened after the composition is applied.

The method of the first of the present invention may involve heating the hair. Such a heating step may involve commonly used heating techniques such as blow drying, or using tongs, straighteners or hoods etc.

The present invention may involve contacting the material with a composition comprising hydroxy-substituted aldehyde once or more than once.

The invention may be used on a regular basis, for example every time hair (or another material) is washed. Alternatively the invention may be used periodically on a less frequent basis, for example, every week or every month.

It has been surprisingly found that the method of the present invention can significantly benefit the hair. This benefit may be a temporary benefit, a permanent benefit or a semi-permanent benefit.

The method and composition of the present invention may benefit the hair by providing improved shine.

The method and composition of the present invention may benefit the hair by providing improved strength.

The method and composition of the present invention may benefit the hair by providing improved thermal protection.

The method and composition of the present invention may benefit the hair by providing permanent waving or straightening under mild conditions.

The method and composition of the present invention may benefit the hair by providing improved manageability and/or combability.

According to a third aspect of the present invention there is provided the use of a hydroxy-substituted aldehyde to enhance at least one property of hair. Preferred features of the third aspect are as defined in relation to the first and second aspects.

One especially preferred compound for use in the present invention is 2-hydroxyoctanal.

According to a fourth aspect of the present invention there is provided the compound of formula

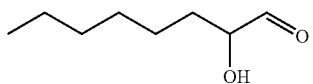

According to a fifth aspect there is provided a method of preparing a compound of the fourth aspect.

The compound of the fifth aspect may be prepared by any suitable method. Such methods will be known to the person skilled in the art. One suitable method is described in example 1.

According to an seventh aspect of the present invention there is provided a composition comprising a compound of the sixth aspect.

Preferably the composition is a hair care composition and preferred features are as defined in relation to the second aspect.

The invention will now be further defined with reference to the following non-limiting examples.

Example 1

The hydroxy-substituted aldehyde compounds used in the present invention were prepared using the following method:

These are formed from corresponding 1,2-diol compounds by selective oxidation of the alpha alcohol. In a three necked flask, a copper catalyst in a high temperature oil were weighed. The flask was then fitted with side arm, a receiving flask and a water cooled condenser. The reaction was heated with stirring to the correct temperature under a flow of nitrogen and/or vacuum.

The required alcohol was added continuously at a constant rate. The product was collected by distillation from the reaction mixture. The vacuum or nitrogen was adjusted to ensure the aldehyde was distilled over rapidly to reduce the chance of further oxidation. The exact conditions depend on aldehyde being produced. A yield of greater than 75% is typical.

Example 2

The permanent/semi-permanent hair conditioning effect of a composition according to the present invention was assessed as follows:

Method 1. 15.2 cm/3 g bleached straight hair tresses were pre-washed with a standard commercial non-conditioning shampoo and blow dried. Using a Dia-Stron® MTT175 miniature tensile tester fitted with the combing accessory, the 'total combing work' of each tress was measured.
2. 2 ml of an aqueous solution containing 1% w/w of 2-hydroxydodecanal and 1% w/w of SLES was applied to the hair tresses, combed through, and left to stand for 5 minutes.
3. The hair tresses were flat ironed with a Tormaline® ceramic hot iron, passing it over the hair tresses slowly five times.
4. The hair tresses were washed and rinsed thoroughly to remove non-bound material from the hair.
5. The hair tresses were blow dried with combing.
6. Again, using a Dia-Stron® MTT175 miniature tensile tester fitted with the combing accessory, the 'total combing work' of each treated hair tress was measured.

Results

After treatment of the tresses according to the invention, the 'total combing work' was reduced by 36.5(±3.5)% (average of two hair tress replicates) compared to the initial value before treatment. This indicates a permanent/semi-permanent hair conditioning effect was conferred. This is believed to be due to reaction of the hair with the 2-hydroxydodecanal.

Example 3

The permanent/semi-permanent hair straightening effect of a composition according to the present invention was assessed as follows:

Method 1. 15.2 cm/3 g bleached straight hair tresses were prewashed with a standard commercial non-conditioning shampoo, combed, hung vertically and allowed to air dry for six hours under ambient conditions, then their initial lengths were measured.
2. For the 'treated' hair tresses, 2 ml of an aqueous solution containing 2% w/w of 2-hydroxyoctanal and 1% w/w of SLES was applied to the hair tresses, combed through and left to stand for 5 minutes.
3. For the control hair tresses, 2 ml of an aqueous solution containing 1% w/w of SLES was applied to the hair tresses, combed through and left to stand for 5 minutes.
4. The hair tresses were flat ironed with a Tormaline® ceramic hot iron, passing it over the tresses slowly five times.
5. The hair tresses were washed and rinsed thoroughly to remove non-bound material from the hair.
6. The hair tresses were combed straight, hung vertically, and allow to air dry for six hours under ambient conditions.
7. The final length of the hair tresses was measured.
8. The degree of straightening was calculated according to the following equation:

$$\% \text{ Straightening} = \frac{L2 - L1}{L0 - L1} \times 100\%$$

Where:
L0=Total straightened length of hair tress
L1=Initial untreated compressed curly length of tress
L2=Final length of tress after straightening, wash, and air dry.

RESULTS

After treatment of the tresses according to the invention, the degree of straightening was 79.2(±5.9)% (average of three hair tress replicates) compared to 21.2(±9.5)% (average of three hair tress replicates) of that of the control tresses. This indicates a permanent/semi-permanent hair straightening effect was conferred. This is believed to be due to reaction of the hair with the 2-hydroxyoctanal.

We claim:

1. A hair care composition comprising an aliphatic hydroxy-substituted aldehyde having a single hydroxyl substitution; wherein the aliphatic hydroxy-substituted aldehyde has at least 3 carbon atoms and the single hydroxyl substitution is at the 2 position.
2. The hair care composition according to claim 1 comprising two or more different hydroxy-substituted aldehydes.
3. The hair care composition according to claim 1 wherein the hydroxy-substituted aldehyde is an α-hydroxy aldehyde.
4. The hair care composition according to claim 1 wherein the hydroxy-substituted aldehyde is selected from 2-hydroxypropanal, 2-hydroxyhexanal or 2-hydroxyoctanal.
5. The hair care composition according to claim 2 comprising a first hydroxy-substituted aldehyde having less than 10 carbon atoms and a second hydroxy-substituted aldehyde having 10 or more carbon atoms.
6. The hair care composition according to claim 5 wherein the second hydroxy-substituted aldehyde is selected from 2-hydroxydecanal, 2-hydroxydodecanal and 2-hydroxytetradecanal.
7. The hair care composition according to claim 2 wherein the first hydroxy-substituted aldehyde is selected from 2-hydroxypropanal, 2-hydroxyhexanal or 2-hydroxyoctanal and the second hydroxy-substituted aldehyde is selected from 2-hydroxydecanal, 2-hydroxydodecanal and 2-hydroxytetradecanal.
8. The hair care composition according to claim 1 wherein the composition comprising the hydroxy-substituted aldehyde further comprises an amine salt of a carboxylic acid.
9. The hair care composition according to claim 1 wherein the composition comprising the hydroxy-substituted aldehyde further comprises a polycarboxylic acid derived chelating agent.
10. The hair care composition according to claim 1 wherein the composition comprising the hydroxy-substituted aldehyde further comprises a succinimidyl ester.
11. The hair care composition according to claim 1 wherein the composition comprising the hydroxy-substituted aldehyde further comprises a crosslinking agent comprising two or more maleic acid derived reactive moieties and a linker having two or more amino groups.
12. The hair care composition according to claim 1 wherein the composition is selected from a shampoo composition, a conditioning composition, a hair dyeing/colouring composition, a hair styling composition, a hair permanent waving composition, and a hair permanent straightening/relaxing composition.
13. The hair care composition according to claim 1 wherein the composition comprising the hydroxy-substituted aldehyde further comprises 1 to 30 wt % of one or more surfactants.
14. The hair care composition according to claim 13 wherein the composition comprising 1 to 30 wt % of one or more surfactants comprises one or more anionic surfactants.
15. The hair care composition according to claim 1 which provides one or more benefits selected from increased gloss or shine, improved combability, improved strength, increased softness, reduced protein loss, improved thermal durability, increased chemical resistance, increased waviness and increased straightness.
16. The hair care composition of claim 15 in which the one or more provided benefit is temporary, semi-permanent or permanent.
17. A hair care composition comprising a compound of formula (i.):

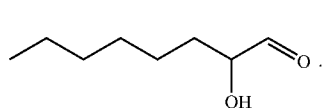

18. A packaged hair colouring product comprising one or more compositions wherein the one or more compositions together comprise a) at least one dye compound and/or one dye precursor compound, and b) the hair care composition of claim 1.

19. The packaged hair colouring product of claim 18 wherein the one or more compositions together further comprise at least one additional component, said at least one additional component selected from the group consisting of an amine salt of a carboxylic acid; a polycarboxylic acid derived chelating agent; a succinimidyl ester; and a cross-linking agent comprising two or more maleic acid derived reactive moieties and a linker having two or more amino groups.

20. The packaged hair colouring product of claim 19 wherein said hair care composition comprises two or more different hydroxy-substituted aldehydes.

* * * * *